US006758862B2

(12) United States Patent
Berry et al.

(10) Patent No.: US 6,758,862 B2
(45) Date of Patent: Jul. 6, 2004

(54) VERTEBRAL BODY AND DISC SPACE REPLACEMENT DEVICES

(75) Inventors: Bret M. Berry, Cordova, TN (US); Eric C. Lange, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 108 days.

(21) Appl. No.: 10/103,237

(22) Filed: Mar. 21, 2002

(65) Prior Publication Data

US 2003/0181980 A1 Sep. 25, 2003

(51) Int. Cl.[7] .................................................. A61F 2/44
(52) U.S. Cl. ............................ 623/17.16; 606/61
(58) Field of Search .............................. 606/61, 57, 72, 606/73; 623/17.11, 17.12, 17.13, 17.14, 17.15

(56) References Cited

U.S. PATENT DOCUMENTS

| | | | |
|---|---|---|---|
| 2,677,369 A | 5/1954 | Knowles | |
| 4,309,777 A | 1/1982 | Patil | |
| 4,599,086 A | 7/1986 | Doty | |
| 4,820,305 A | 4/1989 | Harms et al. | |
| 4,834,757 A | 5/1989 | Brantigan | |
| 5,062,850 A | 11/1991 | MacMillan et al. | |
| 5,147,404 A | 9/1992 | Downey | |
| 5,192,327 A | * 3/1993 | Brantigan | 623/17.11 |
| 5,443,515 A | 8/1995 | Cohen et al. | |
| 5,458,638 A | 10/1995 | Kuslich et al. | |
| 5,458,641 A | 10/1995 | Ramirez Jimenez | |
| 5,534,029 A | 7/1996 | Shima | |
| 5,571,190 A | 11/1996 | Ulrich et al. | |
| 5,609,635 A | 3/1997 | Michelson | |
| 5,609,637 A | 3/1997 | Biedermann et al. | |
| 5,702,451 A | 12/1997 | Biedermann et al. | |
| 5,702,455 A | 12/1997 | Saggar | |
| 5,776,199 A | 7/1998 | Michelson | |
| 5,782,832 A | 7/1998 | Larsen et al. | |
| 5,861,041 A | 1/1999 | Tienboon | |
| 5,865,845 A | 2/1999 | Thalgott | |
| 5,897,556 A | 4/1999 | Drewry et al. | |
| 5,972,031 A | 10/1999 | Biedermann et al. | |
| 5,989,290 A | 11/1999 | Biedermann et al. | |
| 6,086,613 A | 7/2000 | Camino et al. | |
| 6,102,949 A | 8/2000 | Biedermann et al. | |
| 6,106,557 A | 8/2000 | Robioneck et al. | |
| 6,159,211 A | 12/2000 | Boriani et al. | |
| 6,200,348 B1 | 3/2001 | Biedermann et al. | |
| 6,241,771 B1 | 6/2001 | Gresser et al. | |
| 6,245,108 B1 | 6/2001 | Biscup | |
| 6,296,665 B1 | 10/2001 | Strnad et al. | |
| 6,454,806 B1 | * 9/2002 | Cohen et al. | 623/17.15 |
| 6,585,770 B1 | * 7/2003 | White et al. | 623/17.11 |
| 2002/0120338 A1 | * 8/2002 | Boyer III, et al. | 623/17.19 |

FOREIGN PATENT DOCUMENTS

DE 197 38 052 A1 3/1999

* cited by examiner

Primary Examiner—Cary E. O'Connor
Assistant Examiner—Candice C. Melson
(74) Attorney, Agent, or Firm—Woodard, Emhardt, Moriarty, McNett & Henry LLP

(57) ABSTRACT

A vertebral replacement body device for supporting adjacent vertebrae includes a connecting member having an upper member and a lower member engaged thereto at opposite ends thereof. The vertebral replacement body device can have a chamber extending therethrough for fusion of the supported vertebrae.

56 Claims, 7 Drawing Sheets

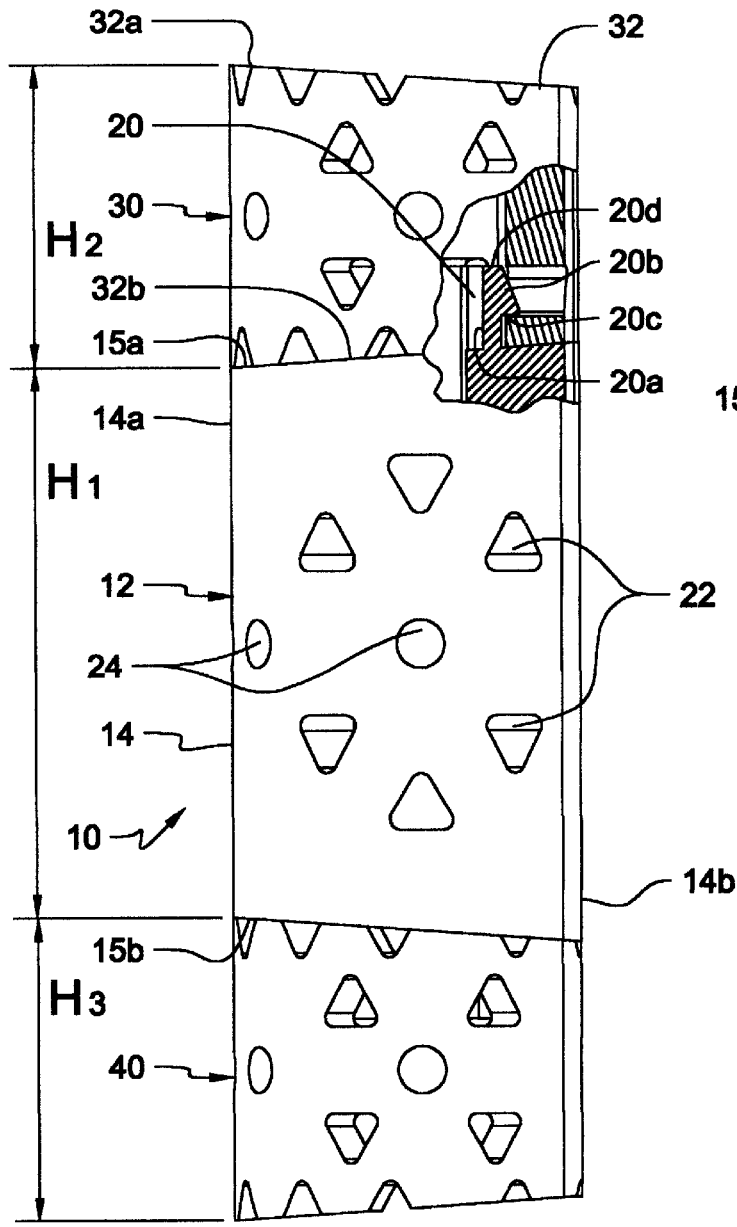
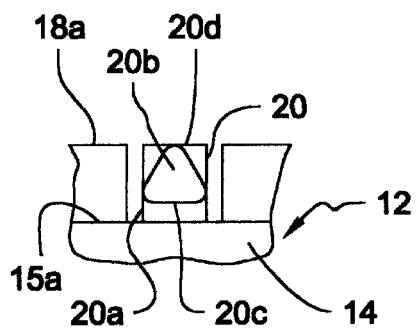
Fig. 4
Fig. 3

VERTEBRAL BODY AND DISC SPACE REPLACEMENT DEVICES

BACKGROUND

The present invention is directed to devices for replacement of one or more vertebral bodies and/or one or more disc spaces between vertebrae of a spinal column.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material.

Devices have also been provided to replace a removed vertebral body and to provide a support structure between the remaining vertebrae on either side of the one or more removed vertebral bodies. One example of such a device is provided in U.S. Pat. No. 5,192,327.

The '327 patent describes oval or hemi-oval rings which can be used in isolation in a disc space or stacked one upon another in interdigitating fashion for replacement of a vertebral body. The rings have ridges along their top and bottom faces that form peaks and valleys to allow the stacked rings to interdigitate when stacked. One problem with these interdigitating ridges is that the stack of rings can slide relative to one another in the direction of the ridges when stacked. The '327 patent also discloses a connecting bar extending through the stacked rings transversely to the ridges to prevent relative sliding between the stacked rings. In order to use the connecting bar in surgery, the surgeon must be provided with a multitude of bars of differing heights and/or "custom fit" the bar as needed for the height of the particular set of stacked cages. In addition, the stacked cages can separate longitudinally even when the connecting bar extends through the stacked cages.

While prior devices are a step in the right direction, there remains a need for improved devices for replacing one or more vertebral bodies and/or one or more disc spaces in a spinal column. The present invention is directed to satisfying these needs, among others.

DESCRIPTION OF THE FIGURES

FIG. 3 is a side elevation view of the vertebral replacement body device of FIG. 1 in partial section to illustrate the interconnection between end members and a connecting member of the device.

FIG. 4 is an elevational view of an engaging member comprising a portion of the connecting member of the device of FIG. 1.

DESCRIPTION OF THE ILLUSTRATED EMBODIMENTS

Figure 1:
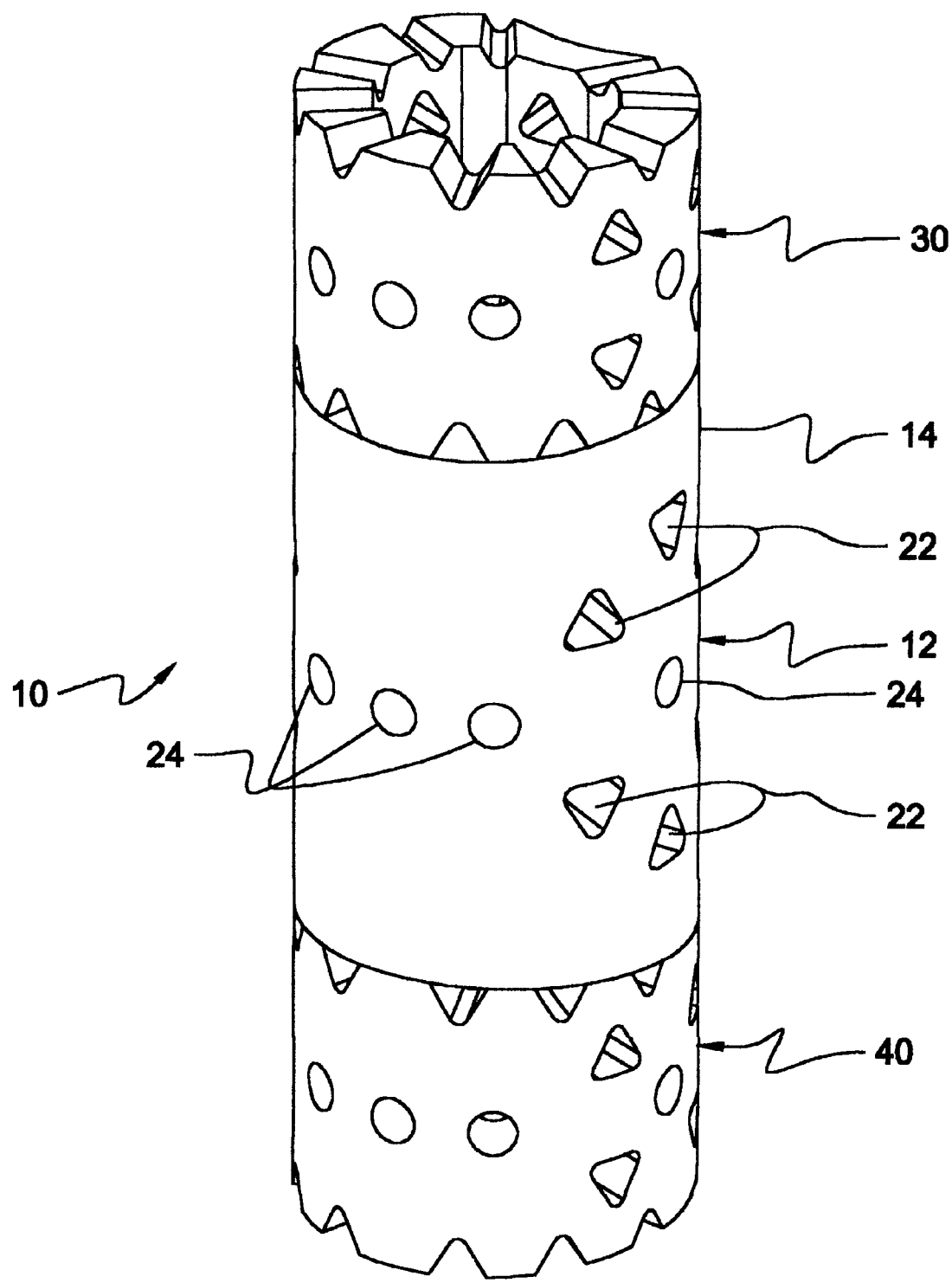
FIG. 1 is a perspective view of a vertebral replacement body device according to one embodiment of the present invention.

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The present invention relates to devices for replacing one or more vertebral bodies in the spinal column and/or one or more disc spaces between adjacent vertebrae. It is contemplated that the vertebral replacement body device will support adjacent ones of the intact vertebrae during fusion thereof. It is further contemplated that one or more components of the vertebral replacement body device can be positioned in a disc space between adjacent vertebrae for supporting the adjacent vertebrae during fusion thereof.

The device can employ current mesh or cage-type devices for engagement with adjacent bony structures, although other types of bone supporting devices are also contemplated. The vertebral replacement body device can have a tubular form with a hollow chamber extending therethrough. The adjacent vertebrae are supported by opposite ends of the device and the chamber can be filled with bone growth inducing or osteogenetic material. The ends of the device include flattened plateau-like end surfaces that can be formed at the junction between bars defining the mesh wall structure of the device.

The vertebral replacement body device includes a middle or connecting member and at least one of an upper member attached to an upper end of the connecting member and/or a lower member attached to a lower end of the connecting member. Each of the upper member, the lower member and the connecting member can have a generally kidney bean cross-sectional shape in the plane transverse to the central axis of the assembled device. Other cross-sectional shapes are also contemplated, including circular, racetrack-shaped, rectangular, square, oval, D-shaped, triangular, or other polygonal shape. Each of the upper member and the lower member can include an interior chamber. The connecting member can also include an interior chamber that generally aligns with the interior chambers of the upper and lower members engaged thereto.

The upper and lower members can be fabricated from a tubular mesh having apertures through its wall. One example of a tubular mesh is provided in U.S. Pat. No. 5,897,556, which is incorporated herein by reference in its entirety. The connecting member can also be fabricated from a tubular mesh. Further forms contemplate that the upper and lower members and the connecting member can be a tubular body with solid walls.

The upper and lower members can be telescopically and non-rotatably engaged with the connecting member. In one embodiment, the connecting member includes an upper extension and a lower extension extending therefrom. The upper and lower extensions are in the form of substantially continuous rings extending around the respective ends of the connecting member. Other forms for the upper and lower extensions are also contemplated. The upper and lower extensions are received in the interior chamber of the respective upper or lower member when the upper and lower members are engaged to the connecting member. In another embodiment, extensions are provided on the upper and lower members, and these extensions are received in an interior chamber or opening at respective ends of the connecting member.

Each of the upper and lower extensions, and each of the chambers of the upper and lower members, can have a non-circular cross-section and interface to prevent relative rotation between the connecting member and the upper or lower member engaged thereto.

The upper and lower extensions of the connecting member each include an engaging member which can be flexed inwardly as the respective upper or lower member is placed around the respective extension of the connecting member. The engaging member fits into an opening or aperture in the inner wall surface of the respective upper and lower member to axially secure the respective upper and lower members to the connecting member.

The vertebral replacement body device can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

Any suitable osteogenetic material or composition is contemplated for placement within the chambers defined by the upper member, the lower member and the connecting member. Such osteogenic material includes, for example, autograft, allograft, xenograft, demineralized bone, synthetic and natural bone graft substitutes, such as bioceramics and polymers, and osteoinductive factors. Where bony material is placed within the chambers of the components of the vertebral replacement body device, the material can be pre-packed into the hollow chambers before the device is implanted, or can be pushed through the plurality of wall openings after the device is in position in the spinal column. A separate carrier to hold the materials within the chambers of the device can also be used. These carriers can include collagen-based carriers, bioceramic materials, such as BIOGLASS®, hydroxyapatite and calcium phosphate compositions. The carrier material can be provided in the form of a sponge, a block, folded sheet, putty, paste, graft material or other suitable form. Moreover, the osteogenetic compositions contained within the vertebral replacement body device can comprise an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agent, held within a suitable carrier material.

Figure 2:
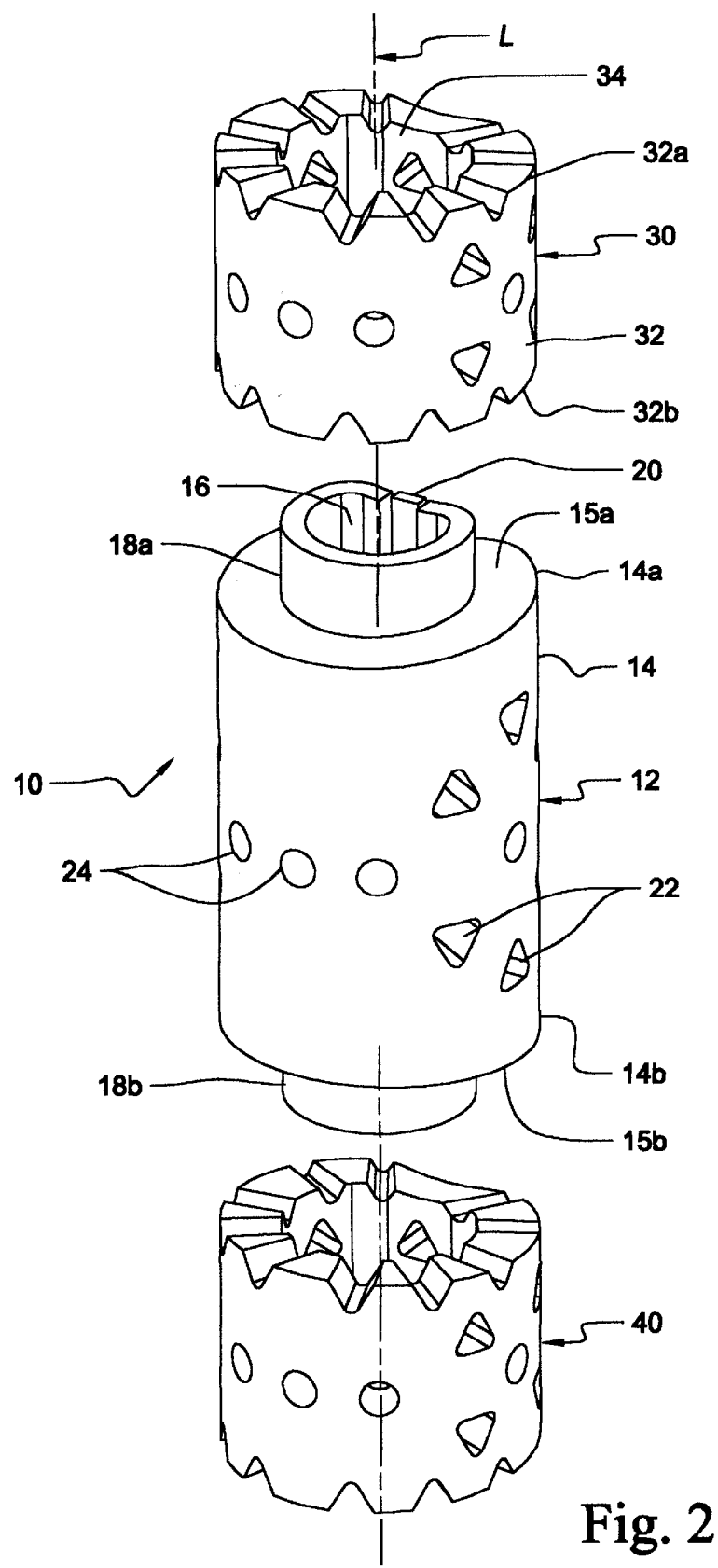
FIG. 2 is an exploded perspective view of the vertebral replacement body device of FIG. 1.

In FIGS. 1–2, a vertebral replacement body device 10 includes a middle or connecting member 12, an upper member 30, and a lower member 40. Device 10 is illustrated as having a tubular form that extends along a longitudinal axis L and defines a chamber extending therethrough along axis L. Bone growth can occur through this chamber for fusion between the vertebral bodies supported at each end of device 10.

Connecting member 12 includes a body 14 extending between an upper end 14a and an opposite lower end 14b. Connecting member 12 further includes an upper extension 18a and a lower extension 18b. Connecting member 12 has an inner wall surface 12a (FIG. 5) that defines a chamber 16 extending between and opening at the outer ends of the extensions 18a, 18b. Each of the extensions 18a, 18b extends outwardly from the respective end 14a, 14b of body 14 and around chamber 16. End surface 15a extends around upper extension 18a, and end surface 15b extends around lower extension 18b. In the illustrated embodiment, extensions 18a, 18b are substantially continuous rings extending from their respective end 14a, 14b. Other embodiments contemplate other forms for the extensions, such as, for example, a series of two or more flexible engaging members (such as engaging member 20 discussed below) or rigid engaging members.

The wall of body 14 includes a number of triangular apertures 22 which extend through the wall and communicate with chamber 16. Other shapes for apertures 22 are also contemplated, including non-circular shapes such as a square, diamond, oval and/or rectangular shapes, circular shapes, and/or polygonal shapes. The wall of body 14 also includes a number of holes 24 extending at least partially therethrough. Holes 24 can be threaded or otherwise sized and/or configured for engagement with one or more insertion instruments (not shown.)

Figure 5:
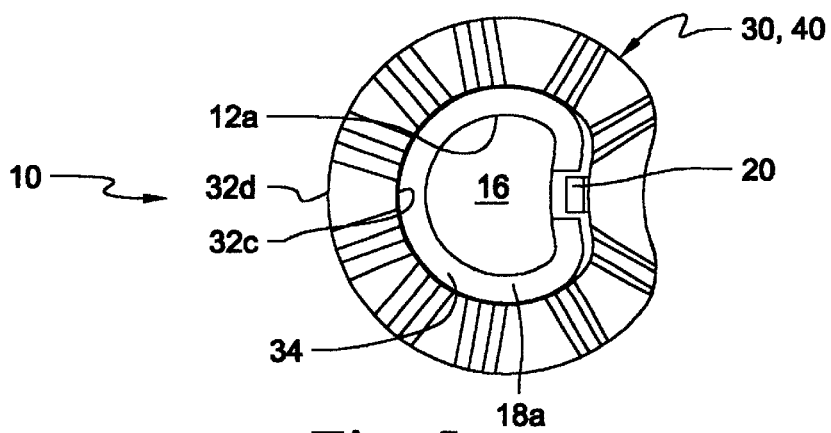
FIG. 5 is an end view of the vertebral replacement body device of FIG. 1.

Referring further to FIGS. 3–5, the substantially continuous wall of each of the extensions 18a, 18b is interrupted by an engaging member 20. Only engaging member 20 for upper extension 18a is illustrated, it being understood that lower extension 18b can also be provided with an identical or similar engaging member. Engaging members 20 secure upper member 30 and lower member 40 to respective ends of connecting member 12, resisting axial dislocation of upper member 30 and lower member 40 away from connecting member 12 along axis L. Engaging members 20 can also resist axial rotation of upper and lower members 30, 40 relative to connecting member 12 about axis L. Other embodiments contemplate that more than one engaging member 20 is provided in the wall of one or both of the extensions 18a, 18b. Further embodiments contemplate that wall of one or both of the extensions 18a, 18b is not substantially continuous, but rather is continuous or includes a number of discrete wall portions sufficiently spaced and sized about body 14 of connecting member 12 for engagement with upper and lower members 30, 40.

Engaging member 20 includes a projection or engaging portion 20b and a stem 20a connected or integrally formed with end surface 15a of body 14. Stem 20a has a reduced thickness to allow engaging member 20 to deflect inwardly in response to a force applied to engaging portion 20b. Engaging portion 20b projects outwardly from stem 20a and has a triangular shape tapering from an engaging surface 20c to an upper end 20d. Other configurations for engaging member 20 are also contemplated. For example, engaging member 20 can be provided with an engaging portion 20b in the form of a partially spherical or rounded nub, a receptacle, rectangular or polygonal shaped tab or projection. Engaging portion 20b can also correspond to the shape the aperture 22 in which it is received. Engaging member 20 can also be a snap ring, collet, bayonet lock, or surface irregularity that resists axial movement of the engaged upper member 30 and lower member 40 away from connecting member 12 along axis L.

Figure 6:
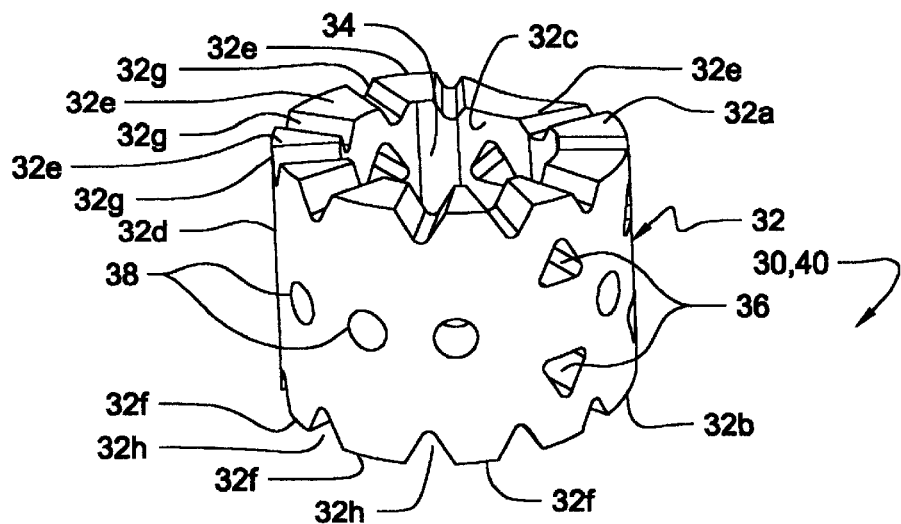
FIG. 6 is a perspective view of an end member comprising a portion of the vertebral replacement body device of FIG. 1.
Figure 7:
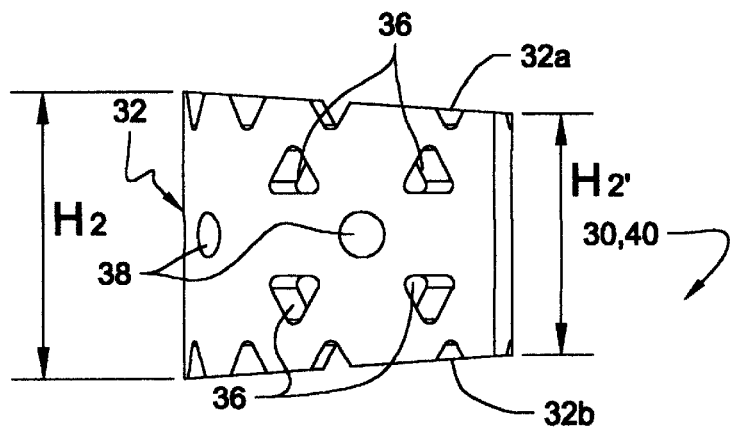
FIG. 7 is an elevation view of the end member of FIG. 6.

Referring also to FIGS. 6–7, upper and lower members 30, 40 are illustrated as being identical, although it is also contemplated that upper member 30 and lower member 40 can be provided with different configurations and/or sizes. With respect to FIGS. 6 and 7, only upper member 30 will be further described, it being understood that lower member 40 can be provided with identical features.

Upper member 30 includes a body 32 extending between an upper end 32a and a lower end 32b. Body 32 has a height H2 between the upper and lower ends 32a, 32b. Height H2 can be selected so that upper member 30 fits within an intervertebral disc space between adjacent vertebrae. Upper end 32a and lower end 32b can be sloped to converge toward one another and form a height H2' opposite height H2. The sloped ends 32a, 32b allow upper member 30 to restore and/or conform to the natural inclination between the adjacent endplates of the vertebral bodies. It is further contemplated that ends 32a, 32b can be parallel to one another.

Body 32 has an inner wall surface 32c defining a chamber 34 that extends between and opens at ends 32a, 32b. As shown in FIG. 5, body 32 has an outer surface 32d that defines a kidney-shaped cross section transverse to longitudinal axis L. Other cross-sectional shapes are also contemplated, including, for example, circular cross-sections and non-circular cross-sections, such as oval, triangular, square, rectangular, polygonal, boomerang shaped, D-shaped, or racetrack shaped cross-sections. In the illustrated embodiment, connecting member 12 has the same cross-sectional shape as the upper and lower members 30, 40 to provide a vertebral replacement body device of uniform cross-sectional shape and size along its height.

Body 32 defines a number of triangular apertures 36 extending at least partially therethrough in communication with chamber 34, and a number of circular holes 38 extending at least partially therethrough from the exterior surface of body 32. Holes 38 or the other holes can be threaded or otherwise sized and/or configured for engagement with one or more insertion instruments.

Body 32 further includes a number of bearing surfaces 32e spaced around first end 32a and bearing surfaces 32f spaced around second end 32b. Adjacent ones of each of the bearing surfaces 32e are separated from one another by V-shaped recesses 32g. Adjacent ones of each of the bearing surfaces 32f are separated from one another by V-shaped recesses 32h. Bearing surfaces 32e, 32f are planar and provide a number of plateau-like, generally flat bearing surfaces spaced about the respective end of body 32. Bearing surfaces 32e, 32f have a trapezoidal shape in the illustrated embodiment, although other shapes are also contemplated. In the illustrated embodiment, ten such bearing surfaces 32e, 32f are provided at each end of body 32. It is also contemplated that fewer than ten or more than ten bearing surfaces could be provided. It is further contemplated that each end of body 32 could be provided with a single, continuous bearing surface extending around chamber 34.

The plateau-like bearing surfaces 32e, 32f provide a surface area about the ends of body 32 for bearing support of the adjacent vertebral endplate and to resist subsidence of body 32 into the vertebrae. The plateau-like bearing surfaces 32e, 32f provide surface area contact between the end of body 32 and the adjacent endplate, providing frictional resistance to body 32 sliding or twisting relative to the adjacent vertebral endplate.

Upper member 30 and lower member 40 are connected to respective ends of connecting member 12 to provide vertebral replacement body device 10. Upper member 30 is advanced over upper extension 18a so that upper extension 18a extends into chamber 34. Engaging member 20 flexes inwardly as inner wall surface 32c of body 32 passes along engaging portion 20b. Engaging portion 20b is configured to reside within one of the apertures 36 extending into the wall of body 32 from chamber 34. When engaging portion 20b and the respective aperture 36 are aligned, engaging member 20 returns towards its pre-insertion position with engaging portion 20b residing in the respective aperture 36. This engages upper member 30 to connecting member 12, resisting movement of upper member 30 away from connecting member 12 along axis L. It is further contemplated engaging surface 20c engages the adjacent lower surface of the respective aperture 36 to provide a positive seat between bearing surface 15a of connecting member 12 and bearing surfaces 32f about end 32b of upper member 30. Lower member 40 is secured to lower extension 18b in a similar manner.

Bearing surfaces 32f at lower end 32b of upper member 30 bear against end surface 15a extending about upper extension 18a of connecting member 12. This bearing relationship transmits the spinal column load from upper member 30 to connecting member 12. The bearing surfaces of the lower member 40 similarly bear against end surface 15b extending about lower extension 18b of connecting member 12. The end surfaces 15a, 15b at the ends of body 14 and the adjacent bearing surfaces of the upper and lower members 30, 40 do not interdigitate. This bearing relationship eliminates stress concentrations and shifting of the components of device 10 that might result from improperly aligned interdigitating surfaces.

Axial rotation of upper member 30 and lower member 40 relative to connecting member 12 is resisted by the interface between upper and lower extensions 18a, 18b and the respective inner wall surface of the upper and lower members 30, 40. In the illustrated embodiment, extensions 18a, 18b have a non-circular shape, such as the kidney shape shown in FIG. 5. Similarly, the inner wall surface 32c of upper member 30 and also the inner wall surface of lower member 40 have a non-circular shape sized to receive in form fitting engagement the respective upper or lower extension 18a, 18b. This non-circular form fitting engagement prevents rotation of upper member 30 and lower member 40 relative to connecting member 12.

Device 10 can be used to replace a vertebra that has been removed from the spinal column segment using known techniques. Device 10 is assembled by securing upper member 30 to one end of connecting member 12 and securing lower member 40 to the other end of connecting member 12. This provides a vertebral replacement body device 10 that has an overall height that is equal to the sum of the heights H1 of body 14, height H2 of upper member 30, and height H3 of lower member 40 (FIG. 3.)

Figure 8:
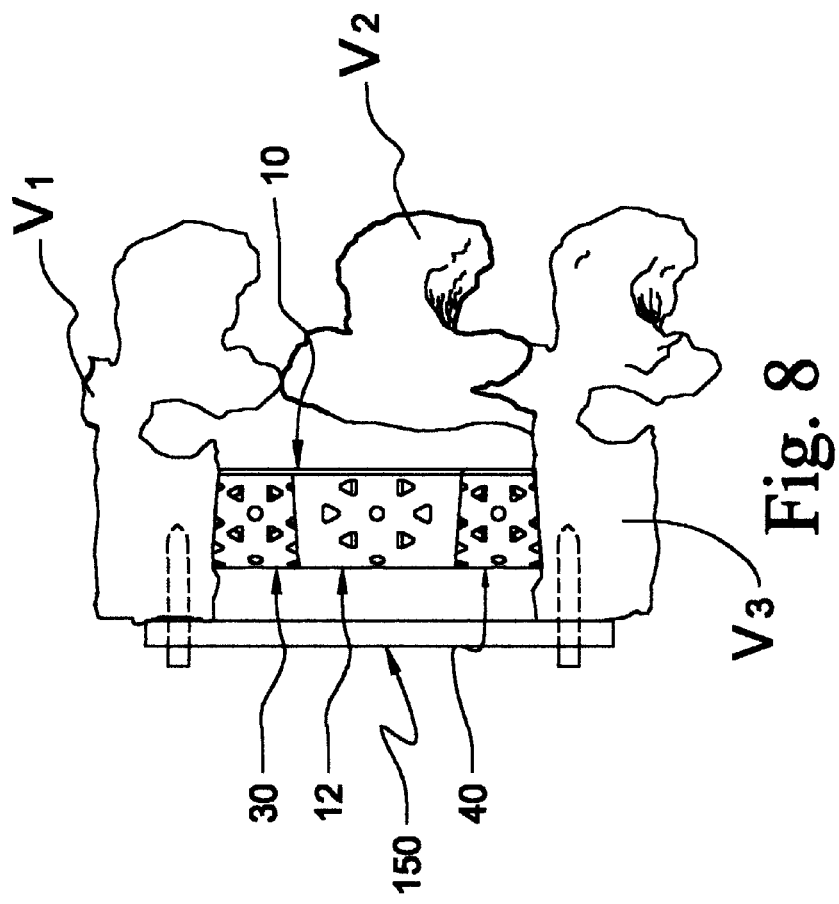
FIG. 8 is an elevational view of the vertebral replacement body device of FIG. 1 positioned in the spinal column between two vertebrae.

As shown in FIG. 8, the assembly 10 can be placed between vertebra V1 and vertebra V3 after removal of vertebra V2. Replacement of more than one vertebra is also contemplated. Although not required, it is contemplated that height H1 could be representative of that of the removed vertebra and heights H2, H3 could be representative of the heights of the respective disc spaces between the removed vertebra V2 and the remaining vertebrae V1, V3. Also shown in FIG. 8 is a stabilization construct 150 engaged to and extending between vertebrae V1 and V3 to support and stabilize the spinal column segment before, during and, if construct 150 is non-resorbable and left in the patient, after fusion. Stabilization construct 150 can be a rod system, plate system or artificial ligament system. It is further contemplated that stabilization system could be attached to any portion of vertebrae V1 and V3, including the anterior, antero-lateral, lateral, postero-lateral or posterior portions.

It is also contemplated that heights H2 and H3 could be identical or different, and that the ends of upper and lower members 30, 40 could be provided with the same or differing angles of inclination. It is further contemplated that device 10 can comprise a kit having a number of upper members 30 and lower members 40 of various sizes and heights H2, H3. A kit could also include a number of connecting members 12 of various sizes and heights H1. Such a kit would provide the surgeon flexibility in selecting the appropriately size and height for members of a device 10 based on conditions encountered in surgery.

Figure 9:
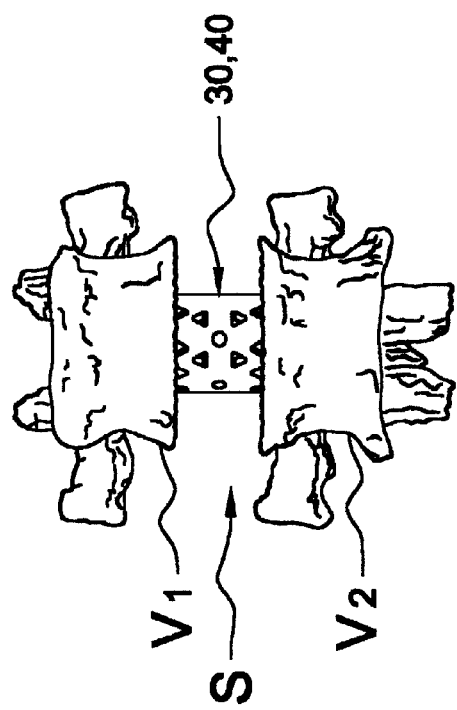
FIG. 9 is an elevational view of one of the end members comprising a portion of the vertebral replacement body device of FIG. 1 positioned in a spinal disc space between adjacent vertebrae.

FIG. 9 illustrates placement of one of the upper or lower members 30, 40 in disc space S between adjacent vertebrae V1, V2 to function as an interbody fusion device. Engagement of stabilization construct to vertebrae V1 and V2 is also contemplated.

It is also contemplated that connecting member 12 could be provided with one end configured to bear against a vertebral endplate, and that only one of the upper and lower members 30, 40 is engaged to the other end of connecting member 12. The assembled device could then be placed between adjacent vertebrae with an end of connecting member 12 and an end of the selected upper or lower member 30, 40 in contact with the adjacent vertebral endplates.

Figure 10:
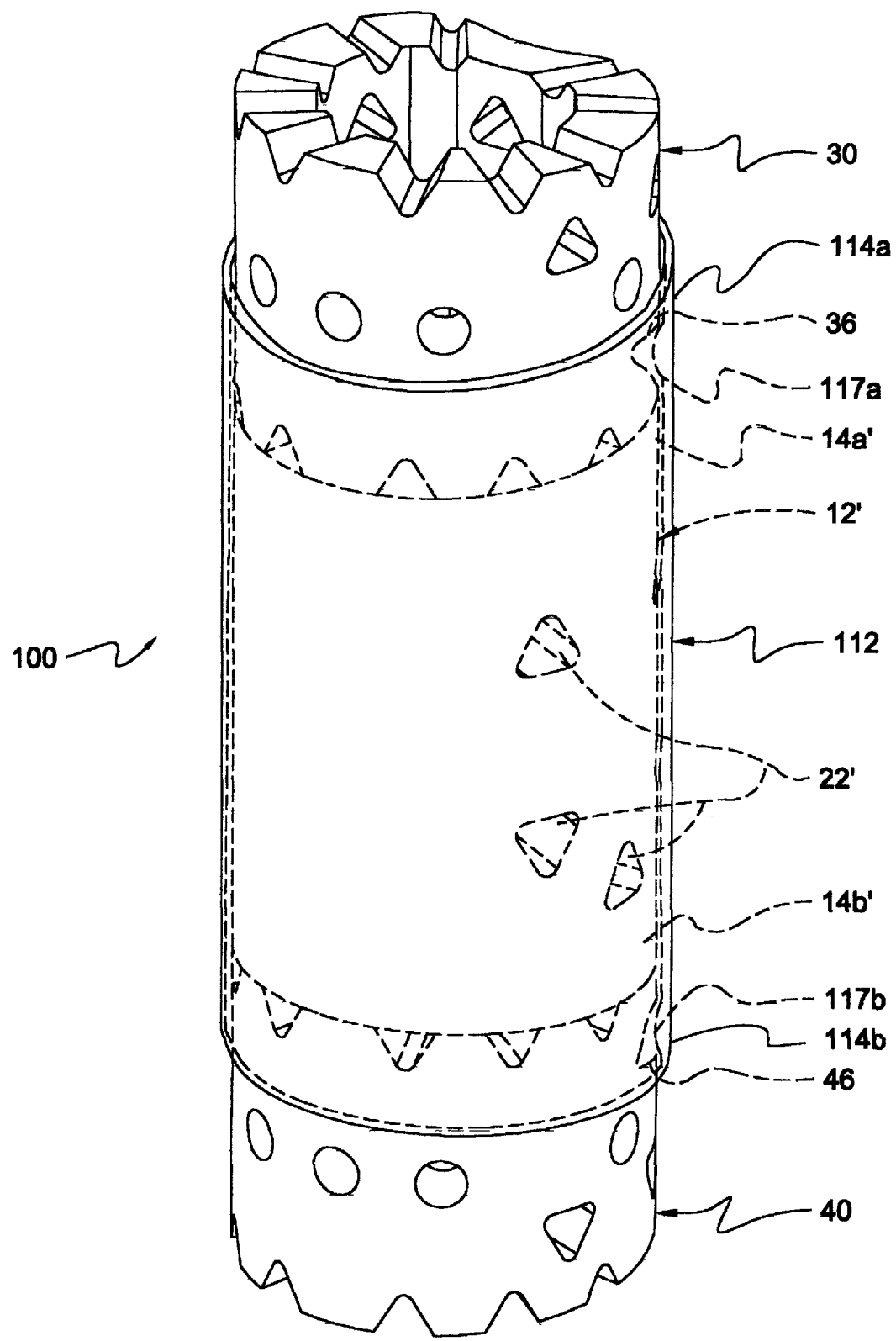
FIG. 10 is a perspective view of another embodiment vertebral replacement body device.

In FIG. 10 there is provided an alternate embodiment vertebral replacement body device 100. Device 100 includes upper member 30 and lower member 40 engaged at opposite ends of a connecting member 12', which can be similar to connecting member 12 discussed above. Connecting member 12' does not include upper and lower extensions extending from end 14a' and 14b'. To secure upper member 30 and lower member 40 to connecting member 12', a sleeve 112 is provided around connecting member 12' that has an upper end 114a overlapping upper member 30 and a lower end 114b overlapping lower member 40.

Sleeve 112 can be provided with engaging members 117a, 117b in the form of projections, engaging members, tabs or the like on its inner wall surface. Engaging members 117a, 117b engage apertures 36, 46 or other receptacle or detent in the outer wall surfaces of upper member 30 and lower member 40, respectively. Engaging members could also be provided to engage apertures 22' or other receptacle or detent in connecting member 12'. So engaged, sleeve 112 resists axial movement of upper member 30 and lower member 40 relative to connecting member 12'.

It is further contemplated that rotation of upper member 30 and lower member 40 relative to connecting member 12' could be prevented by a non-circular, telescoping interface between the members such as discussed above. In another embodiment, rotation of upper member 30 and lower member 40 relative to connecting member 12' could be prevented by the engagement of sleeve 112 with the upper and lower members 30, 40 and, if so configured, with connecting member 12'. In yet a further form of the embodiment of FIG. 10, the connecting member 12' could be integral with sleeve member 112 to provide upper and lower bearing surfaces within sleeve 112 for support of upper member 30 and lower member 40 thereon.

Figure 11:
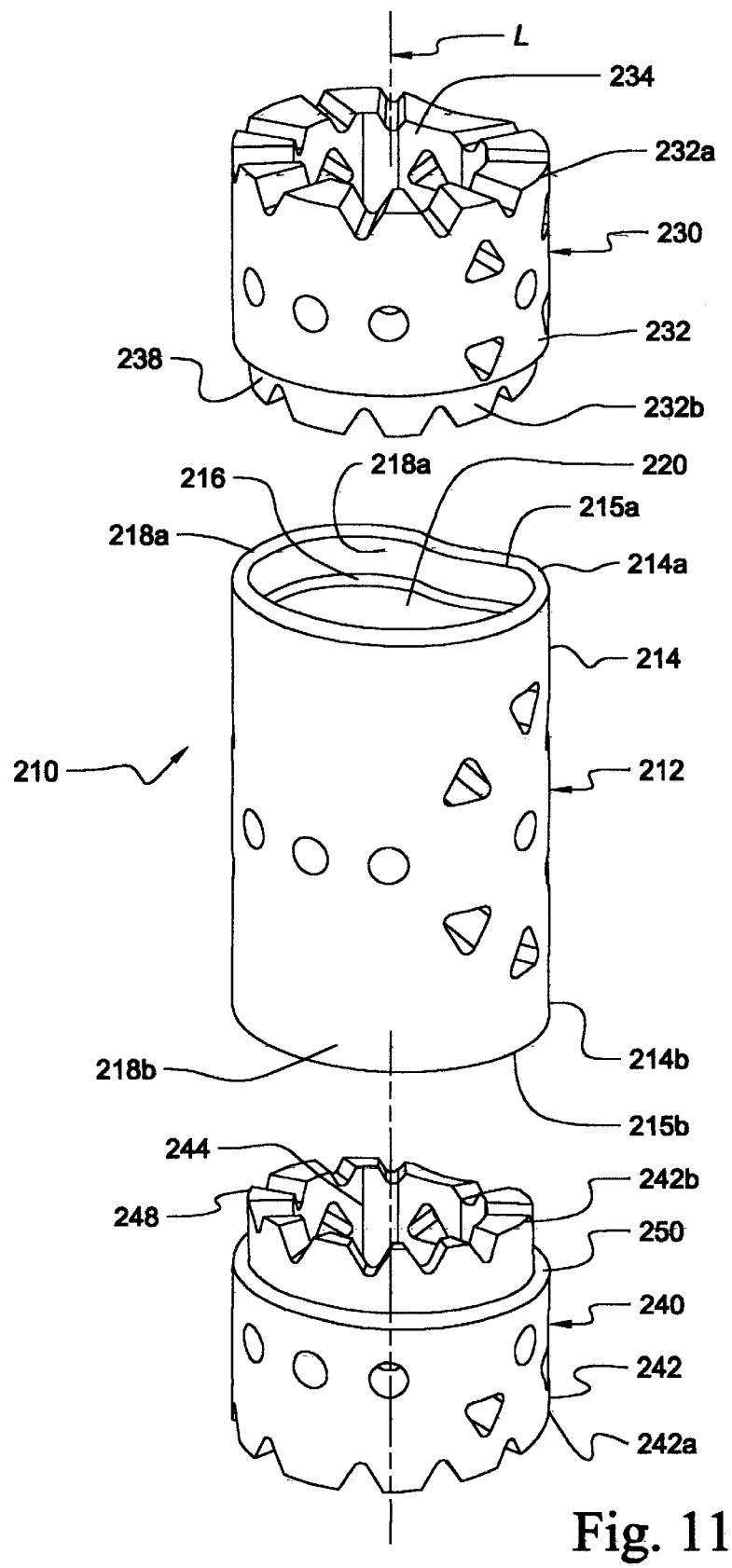
FIG. 11 is an exploded perspective view of another embodiment vertebral replacement body device.

Referring now to FIG. 11, another embodiment vertebral replacement body device 210 is shown. Device 210 includes a connecting member 212 having a body 214 extending between an upper end 214a and a lower end 214b. Upper end 214a includes an upper extension 218a having an end surface 215a therearound. Extension 218a extends around a bearing surface 216 at the upper end of chamber 220. Bearing surface 216 is positioned below end surface 215a in chamber 220. Second end 215b similarly includes an extension 218b having an end surface 215b, and a bearing surface (not shown) at the lower end of chamber 220 below end surface 215b.

Upper member 230 includes a body 232 having an upper end 232a and a lower end 232b. Body 232 extends around a chamber 234. Lower member 240 includes a body 242 having a lower end 242a and an upper end 242b. Body 242 extends around a chamber 244. Lower member 240 includes an inset wall 248 extending around chamber 244, and a bearing surface 250 extending around body 242 below inset wall 248. Upper member 230 similarly includes an inset wall 238 and a bearing surface (not shown) extending around body 232 above inset wall 238.

When assembled, inset wall 238 of upper member 230 is received in chamber 220 of connecting member 212 with extension 218a extending around inset wall 238. Similarly, inset wall 248 of lower member 240 is received in chamber 220 of connecting member 212 with extension 218b extending around inset wall 248. It contemplated that end surface 215a can contact the bearing surface extending around inset wall 238, and that end surface 215b can contact bearing surface 250 extending around inset wall 248. Additionally or alternatively, the lower end of inset wall 238 can contact bearing surface 216 in chamber 220 at the upper end of connecting member 212, and the upper end of inset wall 248 can contact the bearing surface (not shown) in chamber 220 at the lower end of connecting member 212.

Connecting member 212 and/or upper and lower members 230, 240 could be provided with engaging members or a sleeve such as discussed above to prevent axial and/or rotational movement of upper and lower members 230, 240 relative to connecting member 212 when device 210 is assembled. In a further embodiment, connecting member 212 does not include the upper bearing surface 216 and the lower bearing surface in chamber 220 since extensions 218a, 218b are not provided on connecting member 212. In this embodiment, inset walls 238 and 248 are received in chamber 220 at the respective end of connecting member 212, and end surfaces 215, 215b contact respective ones of the bearing surfaces extending around inset walls 238, 248.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A vertebral replacement body device, comprising:
an upper member having a first end for engaging an endplate of an upper vertebral body and an opposite second end, said upper member having a wall defining a chamber extending between said first end and said second end;
a lower member having a first end for engaging an endplate of a lower vertebral body and an opposite second end, said lower member having a wall defining a chamber extending between said first end and said second end; and
a connecting member positionable between said upper member and said lower member, said connecting member having a chamber extending therethrough and including a body having an upper end and a lower end, said connecting member further including an upper extension at said upper end of said body and a lower extension at said lower end of said body, said upper extension including a flexible upper engaging member having a projection engageable with said wall of said upper member and said lower extension including a flexible lower engaging member having a projection engageable with said wall of said lower member.

2. The device of claim 1, wherein:
said upper extension is positionable in said chamber of said upper member such that said upper member is non-rotatably engaged with said connecting member; and
said lower extension is positionable in said chamber of said lower member such that said lower member is non-rotatably engaged with said connecting member.

3. The device of claim 1, wherein said upper extension and said lower extension are each a substantially continuous ring member interrupted by said respective engaging member.

4. The device of claim 1, wherein each of said upper and lower engaging members flexes inwardly toward said chamber of said connecting member as respective ones of said upper member and said lower member are engaged to said connecting member.

5. The device of claim 1, wherein said upper engaging member is integrally formed with said upper end of said body of said connecting member and said lower engaging member is integrally formed with said lower end of said body of said connecting member.

6. The device of claim 1, wherein said upper end of said body of said connecting member defines an upper end surface extending about said upper extension and said lower end of said body of said connecting member defines a lower end surface extending about said lower extension, said upper extension projecting beyond said upper end surface and said lower extension projecting beyond said lower end surface.

7. The device of claim wherein:
said second end of said upper member includes a series of flattened end surfaces spaced therearound for bearing against said upper end surface of said connecting member; and
said second end of said lower member includes a series of flattened end surfaces spaced therearound for bearing against said lower end surface of said connecting member.

8. The device of claim 1, wherein:
said upper member includes at least one aperture extending through said wall of said upper member; and
said lower member includes at least one aperture extending through said wall of said lower member.

9. The device of claim 8, wherein each of said upper and lower engaging members includes an engaging portion positionable in said at least one aperture of respective ones of said upper member and said lower member.

10. The device of claim 9, wherein each of said upper and lower engaging members includes an engaging surface that engages a surface of said at least one aperture to resist axial displacement of respective ones of said upper member and said lower member relative to said connecting member.

11. The device of claim 10, wherein each said at least one apertures of said upper member and said lower member has a triangular shape and each of said engaging portions has a triangular shape sized to fit within said at least one aperture.

12. A vertebral replacement body device, comprising:
an upper member having a first end for engaging an endplate of an upper vertebral body and an opposite second end, said upper member defining a chamber extending between said first end and said second end;
a lower member having a first end for engaging an endplate of a lower vertebral body and an opposite second end, said lower member defining a chamber extending between said first end and said second end;
a connecting member between said upper member and said lower member, said connecting member including a chamber extending therethrough and including a body having an upper end and a lower end, said connecting member further including an upper extension at said upper end of said body and a lower extension at said lower end of said body, said upper extension being positionable in said chamber of said upper member such that said upper member is non-rotatably engaged with said connecting member and said lower extension being positionable in said chamber of said lower member such that said lower member is non-rotatably engaged with said connecting member, wherein:
said upper extension includes a flexible engaging member having a projection engageable with an opening in a wall of said upper member; and
said lower extension includes a flexible engaging member having a projection engageable with an opening in a wall of said lower member.

13. The device of claim 12, wherein:
said chamber of said upper member and said chamber of said connecting member align with one another when said upper member is engaged to said connecting member; and
said chamber of said lower member and said chamber of said connecting member align with one another when said lower member is engaged to said connecting member.

14. The device of claim 12, wherein:
the vertebral replacement body device has a longitudinal axis extending therethrough; and
said upper member, said lower member and said connecting member each have a kidney shaped cross-section transverse to said longitudinal axis.

15. The device of claim 12, wherein said upper member, said connecting member and said lower member are comprised of resorbable material selected from the group consisting of: hard tissues, connective tissues, demineralized bone matrix, polylactide, polyglycolide, tyrosine-derived polycarbonate, polyanhydride, polyorthoester, polyphosphazene, calcium phosphate, hydroxyapatite, bioactive glass, and combinations thereof.

16. The device of claim 12, further comprising a stabilization construct extending between and engaged to the upper vertebral body and the lower vertebral body.

17. The device of claim 12, wherein:
said vertebral replacement body has a longitudinal axis extending therethrough;
said upper extension has a non-circular shape transverse to said longitudinal axis; and
said lower extension has a non-circular shape transverse to said longitudinal axis.

18. The device of claim 17, wherein:
said chamber of said upper member has a non-circular cross-sectional shape transverse to said longitudinal axis and said upper extension is received in said chamber in form fitting engagement with an inner wall surface of said upper member; and
said chamber of said lower member has a non-circular cross-sectional shape transverse to said longitudinal axis and said lower extension is received in said chamber in form fitting engagement with an inner wall surface of said lower member.

19. The device of claim 12, wherein said upper end of said body of said connecting member defines an upper end surface extending radially about said upper extension and said lower end of said body of said connecting member defines a planar surface extending radially about said lower extension, said upper extension projecting beyond said upper end surface and said lower extension projecting beyond said lower end surface.

20. The device of claim 19, wherein:
said second end of said upper member includes a series of flattened end surfaces spaced therearound for bearing against said upper end surface of said connecting member; and
said second end of said lower member includes a series of flattened end surfaces spaced therearound for bearing against said lower end surface of said connecting member.

21. The device of claim 12, wherein said upper member, said connecting member and said lower member are comprised of non-resorbable material selected from the group consisting of: non-reinforced polymers, carbon-reinforced polymer composites, PEEK, PEEK composites, shape-memory alloys, titanium, titanium alloys, cobalt chrome alloys, stainless steel, ceramics and combinations thereof.

22. The device of claim 21, wherein said upper member, said connecting member and said lower member are each comprised of PEEK material.

23. The device of 12, further comprising bone growth material in said chamber of each of said upper member, said connecting member and said lower member.

24. The device of claim 23, said bone growth material includes one or more selected from group consisting of: bone morphogenetic protein, transforming growth factor β1, insulin-like growth factor 1, platelet-derived growth factor, fibroblast growth factor, and LIM mineralization protein (LMP).

25. The device of claim said bone growth material is provided in a carrier having a form selected from the group consisting of: a sponge, a block, folded sheet, putty, and paste.

26. The device of claim 12, wherein
said upper member has a wall extending about said chamber, said wall defining a plurality of openings therethrough communicating with said chamber; and
said lower member has a wall extending about said chamber, said wall defining a plurality of openings therethrough communicating with said chamber.

27. The device of wherein said connecting member includes a chamber extending therethrough and said body of said connecting member includes a wall extending around said chamber, said wall including a plurality of openings therethrough in communication with said chamber of said connecting member.

28. The device of claim 26, wherein at least one of said plurality of openings of each of said upper member and said lower member has a triangular shape.

29. The device of claim 12, wherein:
said first end of said upper member includes a series of flattened end surfaces spaced therearound for bearing against the endplate of the upper vertebral body; and
said first end of said lower member includes a series of flattened end surfaces spaced therearound for bearing against the endplate of the lower vertebral body.

30. The device of claim 29, wherein said flattened end surfaces of each of said upper member and said lower member have a trapezoidal shape.

31. The device of claim 29, wherein said flattened end surfaces of each of said upper member and lower member extend generally parallel to an adjacent vertebral endplate.

32. A vertebral replacement body device, comprising:
an upper member having a first end for engaging an endplate of an upper vertebral body and an opposite second end, said upper member having a wall defining a chamber extending between said first end and said second end;
a lower member having a first end for engaging an endplate of a lower vertebral body and an opposite second end, said lower member having a wall defining a chamber extending between said first end and said second end;
a connecting member positionable between said upper member and said lower member, said connecting member having a body with an upper end and a lower end, said connecting member further including an upper extension at said upper end of said body and a lower extension at said lower end of said body, wherein said upper extension includes a flexible upper engaging member having a projection engageable with said wall of said upper member and said lower extension includes a flexible lower engaging member having a projection engageable with said wall of said lower member, wherein:
said upper end of said body of said connecting member includes an upper end surface adjacent to said upper extension;
said lower end of said body of said connecting member includes an end surface adjacent to said lower extension;
said second end of said upper member includes an end surface bearing against said upper end surface of said connecting member; and
said second end of said lower member includes an end surface bearing against said lower end surface of said connecting member.

33. The device of claim therein said second end of said upper member includes a series of flattened end surfaces spaced therearound; and
said second end of said lower member includes a series of flattened end surfaces spaced therearound.

34. The device of claim 32, wherein said upper engaging member is integrally formed with said upper end of said body of said connecting member and said lower engaging member is integrally formed with said lower end of said body of said connecting member.

35. The device of claim 32, wherein each of said upper and lower engaging members includes an engaging portion forming said projection.

36. The device of claim 32, wherein each of said upper and lower engaging members includes an engaging surface that engages a surface of at least one aperture in said wall of each of said upper member and said lower member to resist axial displacement of said upper member and said lower member relative to said connecting member.

37. The device of claim 32, said upper member is telescopically and non-rotabably positionable about said upper extension and said lower member is telescopically and non-rotatably positionable about said lower extension.

38. The device of claim 32, wherein said upper member is telescopically and non-rotabably positionable within said upper extension and said lower member is telescopically and non-rotatably positionable within said lower extension.

39. The device of claim 32, further comprising a sleeve about said connecting member and at least a portion of said upper member and said lower member, said sleeve engaging at least said upper member and said lower member to maintain said end surfaces of said upper and lower members in contact with a respective one of said upper and lower end surfaces of said connecting member.

40. A vertebral replacement body device, comprising:
an upper member having a first end for engaging an endplate of an upper vertebral body and an opposite second end, said upper member having a wall defining a chamber extending between said first end and said second end;
a lower member having a first end for engaging an endplate of a lower vertebral body and an opposite second end, said lower member having a wall defining a chamber extending between said first end and said second end;
a connecting member positionable between said upper member and said lower member, said connecting member having a body with an upper end and a lower end, said connecting member further including an upper extension at said upper end of said body and a lower extension at said lower end of said body, wherein:
said upper end of said body of said connecting member includes an upper end surface adjacent to said upper extension;
said lower end of said body of said connecting member includes an end surface adjacent to said lower extension;
said second end of said upper member includes an end surface bearing against said upper end surface of said connecting member;
said second end of said lower member includes an end surface bearing against said lower end surface of said connecting member; and
a sleeve about said connecting member and at least a portion of said upper member and said lower member, said sleeve engaging at least said upper member and said lower member to maintain said end surfaces of said upper and lower members in contact with a respective one of said upper and lower end surfaces of said connecting member.

41. The device of claim 40, wherein said second end of said upper member includes a series of flattened end surfaces spaced therearound; and
said second end of said lower member includes a series of flattened end surfaces spaced therearound.

42. The device of claim 40, wherein said upper member is telescopically and non-rotabably positionable about said upper extension and said lower member is telescopically and non-rotatably positionable about said lower extension.

43. The device of claim 40, said upper member is telescopically and non-rotabably positionable within said upper extension and said lower member is telescopically and non-rotatably positionable within said lower extension.

44. The device of claim 40, said upper extension includes a flexible upper engaging member having a projection engageable with said wall of said upper member and said lower extension includes a flexible lower engaging member having a projection engageable with said wall of said lower member.

45. The device of claim 44, wherein each of said upper and lower engaging members includes an engaging portion forming said projection.

46. The device of claim 44, wherein said upper engaging member is integrally formed with said upper end of said body of said connecting member and said lower engaging member is integrally formed with said lower end of said body of said connecting member.

47. The device of claim 44, wherein each of said upper and lower engaging members includes an engaging surface that engages a surface of at least one aperture in said wall of each of said upper member and said lower member to resist axial displacement of said upper member and said lower member relative to said connecting member.

48. A vertebral replacement body device, comprising:
an upper member having a first end for engaging an endplate of an upper vertebral body and an opposite second end, said upper member having a wall defining a chamber extending between said first end and said second end;
a lower member having a first end for engaging an endplate of a lower vertebral body and an opposite second end, said lower member having a wall defining a chamber extending between said first end and said second end;
a connecting member positionable between said upper member and said lower member, said connecting member including a body having a chamber extending between an upper end and a lower end of said body, wherein:
said connecting member and said upper member are telescopically and non-rotatably positionable with respect to one another for placement of said second end of said upper member against said upper end of said connecting member;
said connecting member and said lower member are telescopically and non-rotatably positionable with respect to one another for placement of said second end of said lower member against said upper end of said connecting member; and
said connecting member further includes an upper extension at said upper end of said body and a lower extension at said lower end of said body, said upper extension including a flexible upper engaging member having a projection engageable with said wall of said upper member and said lower extension including a flexible lower engaging member having a projection engageable with said wall of said lower member.

49. The device of claim 48, wherein said upper extension and said lower extension are each a substantially continuous ring member interrupted by said respective engaging member.

50. The device of claim 48, wherein said upper member includes a lower extension at said second end of said lower member positionable in said chamber of said connecting member and said lower member includes an upper extension at said second end of said lower member positionable in said chamber of said connecting member.

51. A method for assembling a vertebral replacement body device, comprising:

providing a connecting member having a body extending between an upper end and a lower end;

telescopically and non-rotatably engaging an upper member to the upper end of the connecting member with an end of the upper member in contact with the upper end of the body; and telescopically and non-rotatably engaging a lower member to the lower end of the connecting member with an end of the lower member in contact with the lower end of the body, wherein telescopically and non-rotatably engaging the upper member to the connecting member and telescopically and non-rotatably engaging the lower member to the connecting member includes placing a sleeve about the upper member, the connecting member and the lower member.

52. The method of claim 51, further comprising:

engaging an aperture of the upper member with an engagement member extending from the upper end of the body of the connecting member; and engaging an aperture of the lower member with an engagement member extending from the lower end of the body of the connecting member.

53. The method of claim 51, further comprising:

placing bone growth material in a chamber of said connecting member, a chamber of said upper member, and a chamber of said lower member.

54. The method of claim 51, wherein the vertebral replacement body defines a longitudinal axis and non-rotatably engaging the upper member and the lower member includes providing an interference fit between the connecting member and respective ones of the upper member and lower member about the longitudinal axis.

55. The method of claim 51, wherein telescopically engaging the upper member and the lower member includes positioning a portion of the connecting member in a chamber of each the upper member and the lower member.

56. The method of claim 51, wherein telescopically engaging the upper member and the lower member includes:

positioning a portion of the upper member in a chamber of the connecting member; and positioning a portion of the lower member in a chamber of the connecting member.

* * * * *

UNITED STATES PATENT AND TRADEMARK OFFICE
CERTIFICATE OF CORRECTION

PATENT NO. : 6,758,862 B2
DATED : July 6, 2004
INVENTOR(S) : Bret M. Berry and Eric C. Lange It is certified that error appears in the above-identified patent and that said Letters Patent is hereby corrected as shown below:

<u>Column 9,</u>
Line 54, add -- 6, -- after the word "claim".

<u>Column 11,</u>
Line 55, add -- 23, wherein -- after the word "claim.
Line 66, add -- claim 26, -- after the word "of".

<u>Column 12,</u>
Line 55, delete the word "therein" after the word "claim" and insert -- 32, wherein --.

Signed and Sealed this

Fourteenth Day of December, 2004

JON W. DUDAS
*Director of the United States Patent and Trademark Office*